United States Patent [19]

Mercer et al.

[11] 4,036,851
[45] July 19, 1977

[54] 1,3-DIPHENYL SUBSTITUTED PYRAZOLINES

[75] Inventors: Alec Victor Mercer, Bramhope; John Stephen Oakland, Morley, both of England

[73] Assignee: Sandoz Ltd., Basel, Switzerland

[21] Appl. No.: 543,325

[22] Filed: Jan. 23, 1975

[30] Foreign Application Priority Data

Jan. 29, 1974 United Kingdom ............... 4087/74
May 3, 1974 United Kingdom ............. 19663/74

[51] Int. Cl.² .................................. C07D 231/08
[52] U.S. Cl. ....................... 260/310 D; 252/301.27; 260/311
[58] Field of Search ............ 260/310 D; 252/301.2 W

[56] References Cited

U.S. PATENT DOCUMENTS

| 3,378,389 | 4/1968 | Schellhammer et al. | 260/310 D |
| 3,661,928 | 5/1972 | Rosenberger et al. | 260/310 D |
| 3,690,947 | 9/1972 | Rosch et al. | 260/310 D |
| 3,753,978 | 8/1973 | Adelsberger et al. | 252/301.2 W |
| 3,865,816 | 2/1975 | Mengler | 260/310 D |
| 3,925,367 | 12/1975 | Boehmke et al. | 252/301.2 W |

FOREIGN PATENT DOCUMENTS

| 1,900,349 | 8/1970 | Germany |
| 2,142,564 | 9/1972 | Germany |
| 1,360,490 | 7/1974 | United Kingdom |

*Primary Examiner*—Donald B. Moyer
*Attorney, Agent, or Firm*—Gerald D. Sharkin; Richard E. Vila; Thomas C. Doyle

[57] ABSTRACT

1,3-Diphenyl substituted pyrazolines having, in the 4- or 5-position of the pyrazoline ring, a sulpho group in free acid or salt form, and the use thereof as optical brightening agents, particularly for synthetic polyamide.

24 Claims, No Drawings

1,3-DIPHENYL SUBSTITUTED PYRAZOLINES

The invention relates to sulpho group containing diphenyl pyrazolines.

Thus, according to the invention, there are provided optical brightening agents, being 1,3-diphenyl substituted pyrazolines and having, in the 4- or 5-position of the pyrazoline ring, a sulpho group in free acid or salt form.

Hitherto proposed sulpho group containing 1,3-diphenyl pyrazoline optical brighteners have had the sulpho group or groups bound, directly or indirectly, to the 1-or 3-phenyl substituents. We have now prepared compounds in which the pyrazoline nucleus itself bears a sulpho group, which compounds in general posess relatively high substantivity and activity, particularly when applied to nylon by the so-called "Pad Thermosol" procedure. The compounds also possess good solubility in water.

The 1- and 3-phenyl rings of the compounds of the invention may, as will be appreciated, be substituted, the nature of substituents which may be borne thereby being diverse, having regard to particular properties desired of the compounds, e.g. shade of nuance when applied to the substrate to be brightened, degree of solubility etc. Such substituents may, for example, be those conventional in the art, i.e. not unduly affecting the fluorescing properties of the compounds and/or the application of the compounds on the substrate to be brightened. Particular examples are given herein. Likewise, the available 4- or 5-position (depending on the location of the sulpho group) of the pyrazoline ring may be substituted. Such position, however, is preferably unsubstituted.

In the compounds of the invention, the sulpho group is preferably in the 4-position.

Representative of the compounds of the invention may be given the compounds which, in free acid form, are of formula I,

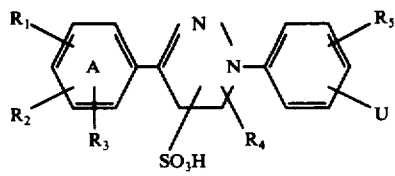

in which either
$R_1$, $R_2$ and $R_3$, independently, each signifies hydrogen, halogen, $C_{1-8}$alkyl, $C_{1-4}$ alkoxy, cyano or —$SO_3H$,
or two of $R_1$, $R_2$ and $R_3$, together, signify a methylenedioxy radical, the other having one of the above significances,
or one of
$R_1$, $R_2$ and $R_3$ signifies a phenyl radical, unsubstituted or substituted by one or two substituents selected from $C_{1-4}$alkyl, $C_{1-4}$alkoxy, halogen and —$SO_3H$, the other two each having one of the significances first mentioned above,
with the proviso that ring A bears no more than one substituent selected from cyano and —$SO_3H$,
$R_4$ signifies hydrogen, $C_{1-8}$alkyl, unsubstituted phenyl or phenyl substituted by one or two substituents selected from halogen, $C_{1-4}$alkyl, $C_{1-4}$alkoxy and —$SO_3H$, $R_5$ signifies hydrogen, halogen, $C_{1-4}$alkyl, $C_{1-4}$alkoxy or cyano,

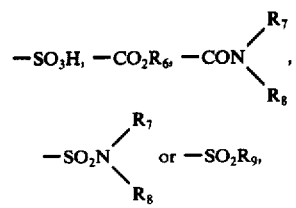

in which $R_6$ signifies hydrogen; $C_{1-4}$alkyl, unsubstituted or substituted by a $C_{1-4}$alkyl, $C_{1-4}$alkoxy, —$SO_3H$, —COOH, $C_{1-4}$alkoxycarbonyl, aminocarbonyl, mono- or di- $C_{1-4}$alkylaminocarbonyl, aminosulphonyl or a mono- or di- $C_{1-4}$alkylaminosulphonyl group; or phenyl, unsubstituted or substituted by one or two substituents selected from $C_{1-4}$alkyl, $C_{1-4}$alkoxy, —$SO_3H$, —COOH, $C_{1-4}$alkoxycarbonyl, aminocarbonyl, and mono- and di-$C_{1-4}$-alkylaminocarbonyl, $R_7$ and $R_8$, independently, each have one of the significances of $R_6$, above, provided that both do not simultaneously signify an unsubstituted or substituted phenyl, $R_9$ signifies hydrogen; $C_{1-4}$alkyl, unsubstituted or substituted by a
i. hydroxy group,
ii. $C_{1-4}$alkyl group,
iii. $C_{1-4}$alkoxy group, unsubstituted or substituted by a $C_{1-4}$alkoxy, —$SO_3H$, —COOH, $C_{1-4}$alkoxycarbonyl, aminocarbonyl or $C_{1-4}$ mono- or di- alkylaminocarbonyl group,
iv —$SO_3H$ group

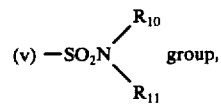

in which $R_{10}$ and $R_{11}$, independently, signify hydrogen or $C_{1-4}$ alkyl,
vi —COOR$_{12}$ group, in which $R_{12}$ signifies hydrogen, $C_{1-4}$alkyl, unsubstituted or substituted by —$SO_3H$, or a phenyl group, unsubstituted or substituted by one or two groups selected from $C_{1-4}$alkyl and —$S_3H$,

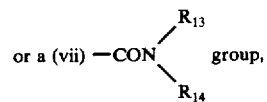

in which $R_{13}$ and $R_{14}$, independently, each have one of the significances of $R_{12}$, above; provided that both do not simultaneously signify an unsubstituted or substituted phenyl; a $C_{2-4}$alkenyl group; a $C_{1-4}$alkoxy group; or a phenyl group, unsubstituted or substituted by one or two substituents selected from $C_{1-4}$alkyl, $C_{1-4}$alkoxy, —$SO_3H$, —COOH, $C_{1-4}$alkoxycarbonyl, aminocarbonyl and mono- and di-$C_{1-4}$alkylaminocarbonyl radicals;
or U has one of the significances of $R_5$, above.

As will be appreciated, the compounds of the invention may be in free acid or salt form. When intended for use as optical brightening agents, as hereinafter described, conventional salt forms such as are used in the optical brightener art may be employed. In general, the cation in the salt form may be any non-chromophoric cation. Preferred cations are the alkali-metal cations, such as of lithium, potassium and sodium, particularly the latter, and ammonium and alkylammonium cations. Preferred such ammonium and alkylammonium cations are of formula $R_{15}R_{16}R_{17}R_{18}N+$ in which $R_{15}$, $R_{16}$, $R_{17}$ and $R_{18}$, independently, each signify hydrogen or $C_{1-4}$alkyl, unsubstituted or substituted by one or two, preferably one, hydroxy groups. As examples may be given the ammonium, mono-, di- and triethanolammonium and mono-, di- and tri-isopropanolammonium cations. The preferred salt forms are the sodium salt forms. As will be appreciated, the salt forms may be obtained from the free acid forms, and vice versa, in conventional manner, and further may be interconverted in conventional manner. For ease of preparation and for stability considerations, the salt forms of the compounds are preferred.

In the compounds of the invention, any alkyl or alkoxy radical, where such is of three or more carbon atoms, may be straight or branched. As examples of alkyl and alkoxy radicals of 1 to 4 carbon atoms may be given the methyl, ethyl, n-propyl, iso-propyl, n-butyl and tert.-butyl alkyl radicals and the methoxy, ethoxy, n-propoxy, iso-propoxy, n-butoxy and tert.-butoxy alkoxy radicals. As examples of alkyl radicals of 1 to 8 carbon atoms may be given the above, together with, for example, the hexyl, heptyl and octyl radicals. Any alkyl radical of 1 to 8 carbon atoms is, however, preferably of 1 to 4 carbon atoms. The more preferred alkyl radicals are the methyl and ethyl radicals, particularly the former. The preferred alkoxy radicals are the methoxy and ethoxy radicals, particularly the former.

As examples of halogen atoms present in the compounds of the invention may be given the fluorine, chlorine and bromine atoms, chlorine being preferred.

In the compounds of formula I, $R_5$ preferably signifies hydrogen. U is preferably in the p-position of the phenyl ring. U preferably signifies CN, $-CO_2R_6$, $-CONR_7R_8$, $-SO_2NR_7R_8$ or $-SO_2R_9$, in which $R_6$, $R_7$, $R_8$ and $R_9$ are as defined above. $R_1$, $R_2$ and $R_3$, independently, preferably signify hydrogen, halogen (particularly chlorine) or $C_{1-4}$alkyl (particularly methyl). $R_4$ preferably signifies hydrogen, $C_{1-4}$alkyl or phenyl, more preferably hydrogen.

Thus, as a preferred class of compounds of the invention may e given those which, in free acid form, are of formula I'

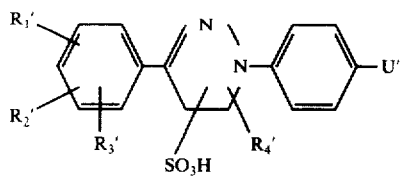

in which
$R_1'$, $R_2'$ and $R_3'$, independently, each signify hydrogen, halogen or $C_{1-4}$alkyl,
$R_4'$ signifies hydrogen, $C_{1-4}$alkyl or phenyl, and
U' signifies CN, $-CO_2R_6$, $-CONR_7R_8$, $-SO_2NR_7R_8$ or $-SO_2R_9$, in which $R_6$, $R_7$, $R_8$ and $R_9$ are as defined above.

In the compounds of formula I and I', U and U', respectively, preferably signify $-CO_2R_6$, $-SO_2NR_7R_8$, $-SO_2R_9$ or CN. Any $R_6$ preferably signifies $C_{1-4}$alkyl, particularly $C_{1-2}$alkyl. Any $R_7$ or $R_8$ in such groups or in any group $-CONR_7R_8$ is preferably hydrogen or $C_{1-4}$alkyl, unsubstituted or substituted by a $-SO_3H$ group, with the proviso that only one $-SO_3H$ group is borne by the group $-CONR_7R_8$ or $-SO_2NR_7R_8$. $R_7$ and $R_8$ more preferably both signify hydrogen. Any $R_9$ in $-SO_2R_9$ is preferably $C_{1-4}$alkyl, more preferably methyl or ethyl and most preferably methyl. The sulpho group attached to the pyrazoline ring is preferably in the 4-position thereof and $R_4$ or $R_4'$ preferably in the 5-position. $R_4'$ in the compounds of formula I' is preferably hydrogen.

As a particularly preferred class of compounds may be given the compounds which, in free acid form, are of formula I''

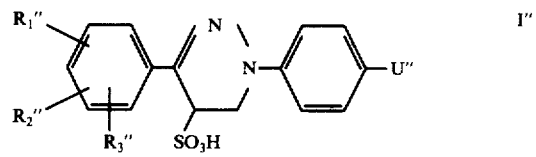

where
$R_1''$, $R_2''$ and $R_3''$, independently, signify hydrogen, chlorine or $C_{1-4}$alkyl (particularly methyl),
U'' signifies CN, $-CO_2R_6''$, $-SO_2NR_7''R_8''$ or $-SO_2R_9''$ in which $R_6''$ signifies $C_{1-4}$, preferably $C_{1-2}$alkyl, $R_7''$ and $R_8''$, independently, signify hydrogen or $C_{1-4}$alkyl, unsubstituted or substituted by a $-SO_3H$-group, with the proviso that a maximum of one $-SO_3H$-group is contained in $-SO_2NR_7''R_8''$, $R_7''$ and $R_8''$ preferably both signifying hydrogen, and $R_9''$ signifies $C_{1-4}$alkyl, preferably $C_{1-2}$alkyl and more preferably methyl.

Still further preferred compounds are those which, in free acid form, are of formula I''',

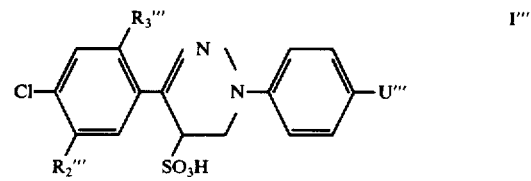

in which
$R_2'''$ signifies hydrogen, chlorine or methyl,
$R_3'''$ signifies hydrogen or methyl, and U''' signifies $-CN$, $-CO_2R_6'''$, $-SO_2NH_2$ or $-SO_2R_9'''$, in which $R_6'''$ signifies $C_{1-2}$alkyl, and
$R_9'''$ signifies $C_{1-2}$alkyl, preferably methyl.

The most preferred significance of U''' is $-SO_2R_9'''$. Also, preferably $R_2'''$ and $R_3'''$ are the same and signify hydrogen or $R_2'''$ signifies chlorine and $R_3'''$ signifies methyl.

The invention also provides a process for the production of the 1,3-diphenyl 4- or 5-sulpho pyrazolines of the invention, which process comprises a. reacting a propiophenone having, or the 2- or 3-position ($\alpha$ or $\beta$ carbon atom) a sulpho group, in free acid or salt form, and on the 3-position a halogen, free amino, dialkylamino, morpholino, piperidino or pyrrolidino radical with a phenylhydrazine, or b. reacting a diphenylnitrile imine (obtainable by treatment of a α-chlorobenzaldehyde phenylhydrazone with base) with a vinyl sulphonic acid in free acid or, preferably, salt form.

More particularly, the invention provides a process for the production of compounds which, in free acid form, are of formula I, above, characterised by ai. reacting a compound of formula II,

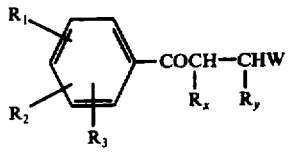

in which $R_1$, $R_2$ and $R_3$ are as defined above, and one of $R_x$ and $R_y$ is $SO_3H$, the other $R_4$, and W signifies a halogen, $-NH_2$, dialkylamino, morpholino, piperidino or pyrrolidino radical, with a compound of formula III,

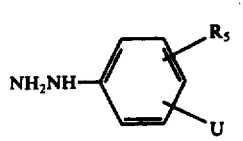

in which $R_5$ and U are as defined above, or bi. reacting a compound of formula IV,

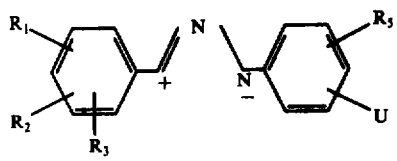

with a compound of formula V,

in which $R_4$ is as defined above, and the wavy line indicates that $R_4$ may be in cis or trans relative position to the $-SO_3H$ group, As will be appreciated, interconversions from one compound of the invention to another are possible. Thus, for example, a compound which, in free acid form, is of formula Ic

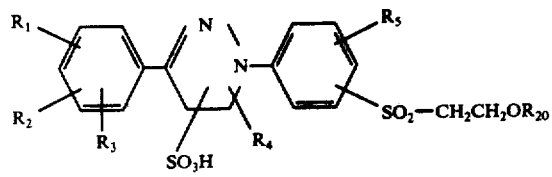

in which $R_1$, $R_2$, $R_3$, $R_4$ and $R_5$ are as defined above, and $R_{20}$ signifies hydrogen or $C_{1-4}$alkyl radical, unsubstituted or substituted by a $C_{1-4}$alkyl, $C_{1-4}$alkoxy, $-SO_3H$ group, COOH, $C_{1-4}$alkoxycarbonyl, aminocarbonyl or $C_{1-4}$ mono or di-alkyl aminocarbonyl, may be obtained by reacting a compound which, is free acid form, is of formula Id,

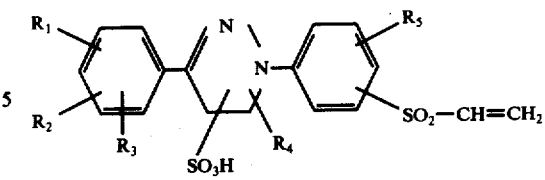

in which $R_1$, $R_2$, $R_3$, $R_4$ and $R_5$ are as defined above, with a compound of formula VI,

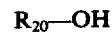

$$R_{20}-OH \quad VI$$

in which $R_{20}$ is as defined above.

Processes a) and ai) are conveniently carried out in water, in a water-miscible solvent, such as ethanol, iso-propanol, acetic acid or dimethylformamide or in a mixture of water and such solvent. A suitable reaction temperature is from 20° to 200° C, preferably 50° to 150° C. The reaction may be carried out at a pH of from 1 to 10, preferably from 4 to 8.

Processes b) and bi) are conveniently carried out in an inert organic solvent, such as cellosolve, or in aqueous organic solvent media, such as in aqueous cellosolve. A suitable reaction temperature is from 0° to 200° C, preferably from 15° to 150° C.

The interconversion, above described for converting a compound of formula Id into a compound of Ic, may be carried out in the presence or absence of solvents, suitable inert solvents, where such are used, being dioxan and dimethylformamide. A suitable temperature is from 20° to 150° C, preferably from 20° to 100° C. The reaction is advantageously carried out in the presence of a basic catalyst, such as sodium hydroxide or sodium carbonate.

The compounds of the invention may be isolated and purified in conventional manner.

The compounds of formulae II, III, IV, V and VI, are known or may be obtained in conventional manner from available starting materials. The compounds of formula Id are, of course, compounds of the invention and, as such, may be prepared by the processes a) and b) above described.

The compounds of the invention are useful as optical brightening agents, giving good results on natural or synthetic polyamide fibres, particularly on nylon 6 and nylon 6,6 fibres. Thus the invention also provides a process for optically brightening a fibrous substrate, preferably of natural or synthetic polyamide fibres, particularly of nylon 6 or nylon 6,6 fibres, comprising applying thereto, as brightening agent, a compound of the invention.

The compounds of the invention may be applied to the polyamide fibres, which may be, for example, in yarn, non-woven, woven or knitted form, in conventional manner, and employing conventional amounts, for example by the so-called "thermosol" application method, (Gunn and Nightingale "Cotton and Man-Made Fibres Year Book" 1966–67, p. 410).

In such process the compounds are applied in an amount of from 0.01% to 0.7%, preferably 0.05% to 0.3%, based on the weight of substrate. The substrate is padded with liquor at a temperature of from 0° to 60° C, preferably 10° to 50° C at a pick-up of from 20 to 120%, preferably 40 to 90%, the liquor containing such additives as surfactants and formic acid etc. as desired. The subsequent heat treatment applied for 5 to 120 secs, preferably 15 to 60 secs, the temperature being 140° to 190° C, preferably 160° to 185° C, for nylon 6, and 140° to 220° C, preferably 170° to 200° C for nylon 6,6.

The compounds give notably bright effects when applied by this method. Other methods include the so-called "acid flash" procedure and exhaust, acid or neutral bath, methods. In all these applications, the compounds are preferably employed in salt form.

The following Examples, in which all parts and percentages are by weight and all temperatures are in degrees centigrade, illustrate the invention.

EXAMPLE 1

17.6 g of the sodium salt of 4'-chloroacetophenone-2-sulphonic acid (Zhur. Obshchei Khim., 29, 949 [1959]), 9.3 g morpholine hydrochloride and 2.3 g paraformaldehyde were added to 60 ml cellosolve. The mixture was refluxed for 1 hour, cooled to 0° and the white precipitate collected by filtration to give 21.6 g of the Mannich base (internal salt).

21.6 g of the crude Mannich base, 12.6 g of p-sulphonamidophenylhydrazine hydrochloride (Gazz. chim. ital. 72, 97 [1942]) and 17.0 g sodium carbonate were added to 150 ml water. The mixture was refluxed for 3 hours, cooled to 0° and the yellow solid collected by filtration. The filter cake was washed and dried to give the pyrazoline:

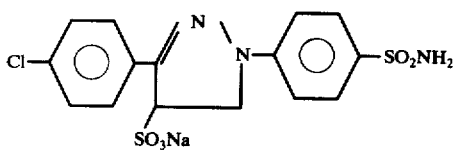

as a pale yellow solid.

EXAMPLE 2

8.68 g 3-(4''-morpholino)-[4'-chloro-2',5'-dimethyl-propiophenone]-2-sulphonate (internal salt - prepared by an analogous procedure to that for the preparation of the Mannich base in Example 1), 4.5 g p-hydrazinophenyl-methyl-sulphone (Belg. Pat. No. 666,407; J. Prakt. Chem. 132, 24 [1931]) and 1.27 g sodium carbonate were added to 40 ml water. The mixture was refluxed for 17 hours, cooled to 0° and the yellow solid collected by filtration. The filter cake was washed and dried to give the pyrazoline:

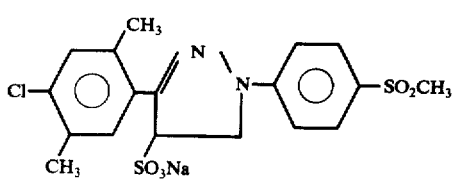

as a white solid.

EXAMPLE 3

By repeating the procedure of Example 1, but using p-hydrazinophenyl-methyl sulphone, the pyrazoline:

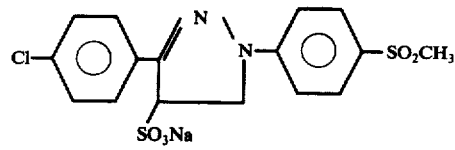

was obtained as a pale yellow solid.

EXAMPLE 4

By repeating the procedure of Example 2, but using p-sulphonamidophenylhydrazine hydrochloride, the pyrazoline:

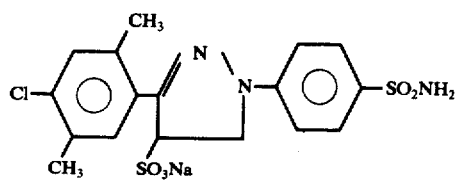

was obtained as a white solid.

EXAMPLE 5

To a solution of 21.6 g α-chlorobenzaldehyde phenylhydrazone (Ber., 27, 2121 [1894]) and 19.5 g sodium vinyl sulphonate in 300 ml cellosolve and 45 ml water was added 27.5 ml tri-ethylamine at 25°. The resulting mixture was stirred at room temperature for 24 hours, filtered and the solvent removed from the filtration to give the pyrazoline:

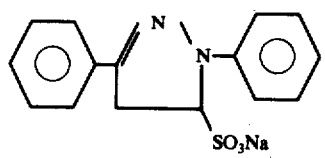

as a pale yellow solid.

By repeating the procedures of Example 1 or 2, using the appropriate starting materials, the following pyrazolines were obtained:

| Expl. No. | Compound | Appearance |
|---|---|---|
| 6 | ![compound] Cl—⌬—C(=N-N-⌬—COOC$_2$H$_5$)—CH(SO$_3$Na) | Pale yellow solid |

| Expl. No. | Compound | Appearance |
|---|---|---|
| 7 | 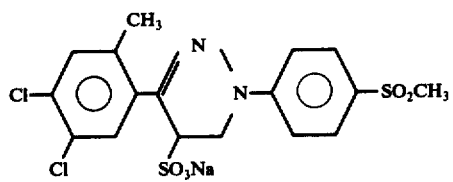 | Pale yellow solid |
| 8 | | Pale yellow solid |

EXAMPLE 9

28.65 g 3-(4"-morpholino)-(4',5-dichloro-2'-methyl-propiophenone)-2-sulphonate (internal salt - prepared by an analogous procedure to that for the preparation of the Mannich base in Example 1, above, 15.81 g p-hydrazino-phenyl-methyl-sulphone and 4.25 g sodium carbonate were added to 110 ml water, the mixture was refluxed for 4 hours, cooled to 0° C and the yellow solid collected by filtration. The filter cake was washed and dried to give the pyrazoline:

as a pale yellow solid.

EXAMPLE 10

By repeating the procedure of Example 9, but using p-sulphonamido phenyl hydrazine hydrochloride, the pyrazoline:

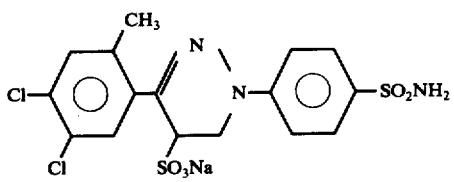

was obtained as a pale yellow solid.

EXAMPLE 11

By repeating the procedure of Example 1, above, but using p-cyanophenyl hydrazine hydrochloride (J. Amer. Chem. Soc., 66 1851, (1944), the pyrazoline:

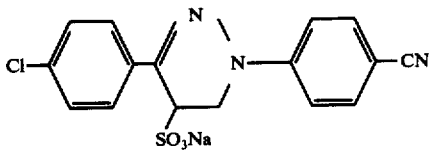

was obtained as a pale yellow solid.

Following the procedure of Example 1 or Example 2 and employing appropriate starting materials, the following compounds are obtained.

| Example | Compound | Appearance |
|---|---|---|
| 12 | Cl—⌬—C(=N-N)—⌬—CONH₂ (SO₃Na) | pale yellow solid |
| 13 | (CH₃, Cl, CH₃)—⌬—C(=N-N)—⌬—CON(CH₃)₂ (SO₃Na) | off white solid |
| 14 | (CH₃, Cl, CH₃)—⌬—C(=N-N)—⌬—CO₂CH₂CH₂OCH₂CH₃ (SO₃Na) | off white solid |

| Example | Compound | Appearance |
|---|---|---|
| 15 | Cl–C₆H₄–C(=N–N(–C₆H₄–CO₂–C₆H₄–SO₃Na))–CH₂ with SO₃Na | pale yellow solid |
| 16 | Cl–C₆H₄–C(=N–N(–C₆H₄–CON(CH₃)CH₂CH₂SO₃Na))–CH₂ with SO₃Na | yellow solid |
| 17 | Cl–C₆H₄–C(=N–N(–C₆H₄–SO₂CH₂CH₂SO₂NH₂))–CH₂ with SO₃Na | pale yellow solid |
| 18 | 2,4-(CH₃)₂-Cl-C₆H₂–C(=N–N(–C₆H₄–CN))–CH₂ with SO₃Na | white solid |
| 19 | 2,4-(CH₃)₂-Cl-C₆H₂–C(=N–N(–C₆H₃–Cl₂))–CH₂ with SO₃Na | off white solid |

EXAMPLE 20

By repeating the procedure of Example 5, but using α-chloro-p-chlorobenzaldehyde-p-methylsulphonylphenylhydrazone (prepared by an analogous procedure to that for the preparation of α-chlorobenzaldehyde phenylhydrazone) the pyrazoline:

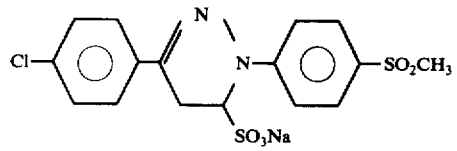

was obtained as a yellow solid.

EXAMPLE 21

By repeating the procedure of Example 1, but using 3-(4''-morpholino)-propiophenone-2-sulphonate (prepared by an analogous procedure to that for the preparation of the Mannich base in that example) and p-hydrazino methylbenzoate, the pyrazoline:

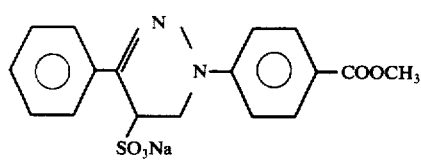

was obtained as a pale yellow solid.

EXAMPLE 22

By repeating the procedure of Example 22, but using phenyl hydrazine, the pyrazoline:

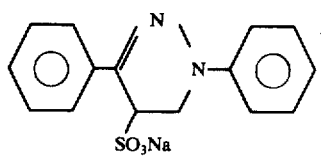

was obtained as a pale yellow solid.

EXAMPLE 23

By repeating the procedure of Example 21, but replacing the sodium vinyl sulphonate used therein by 1-sulpho-prop-1-ene sodium salt, the pyrazoline:

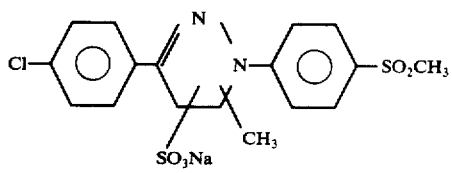

was obtained as a pale yellow solid.

APPLICATION EXAMPLES

A. A strip of white nylon 6,6, 15 cm wide and weighing 8 g, was padded at 100% expression through a solution containing 0.2% of the pyrazoline produced in Example 3, 2% of a non-ionic alkylene oxide adduct of an alkylated phenol, and 0.2% formic acid. The nylon piece ws dried at 80° and then passed through an oven at 180° for 30 seconds. The treated piece showed a brilliant whiteness of neutral hue, compared with the untreated piece.

B. A strip of white nylon 6, 15 cm wide and weighing 8 g, was padded at 100% expression through a solution containing 0.1% of the pyrazoline produced in Example 3, above, of a non-ionic alkylene oxide adduct of an alkylated phenol, and 0.2% formic acid. The nylon piece was dried at 80° and then passed through an oven at 180° for 30 seconds. The treated piece showed a brilliant whiteness of neutral hue, compared with the untreated piece.

C. A strip of nylon 6.6, 15 cm wide and weighing 8 g, was padded at 100% expression through a solution containing 0.1% of the pyrazoline produced in Example 7, above. The nylon piece was boiled for 1 minute in 240 ml water containing 0.2% acetic acid, and was then washed off in boiling water for 1 minute. The piece was then rinsed in cold demineralised water and dried in an oven at 80°. The treated piece showed a brilliant whiteness compared to the untreated piece.

D. A 5 g piece of white nylon 6.6 was treated with 200 ml of a solution containing 25 milligrams of the pyrazolin produced in Example 9, above, and 150 ml of glacial acetic acid. The piece was entered at 40°, the temperature of the bath increased to 90°-100° over 30 minutes and then maintained at 90°-100° for a further 30 minutes. The piece was removed from the bath, rinsed in cold demineralised water and dried in an oven at 80°. The treated piece showed a brilliant whiteness compared to the untreated piece.

What is claimed is:

1. A compound of the formula:

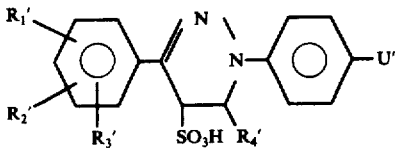

wherein
$R_1'$, $R_2'$ and $R_3'$, independently, are hydrogen, halogen or $C_{1-4}$ alkyl,
$R_4'$ is hydrogen, $C_{1-4}$ alkyl or phenyl, and U' is —COOR$_6$, —CONH$_2$, SO$_2$R$_9$ or SO$_2$NH$_2$ where $R_6$ and $R_9$ are $C_{1-4}$ alkyl.

2. A compound according to claim 1 wherein U' is —SO$_2$R$_9$ or SO$_2$NH$_2$.

3. A compound of claim 1, wherein U' signifies —SO$_2$NH$_2$ or —CONH$_2$.

4. A compound of claim 1, wherein U' signifies —CO$_2$R$_6$.

5. A compound of claim 4, wherein R$_6$ is C$_{1-2}$alkyl.

6. A compound of claim 1, wherein U' signifies —SO$_2$R$_9$.

7. A compound of claim 6, wherein R$_9$ is C$_{1-2}$alkyl.

8. A compound of claim 1, wherein R$_4'$, signifies hydrogen.

9. A compound of claim 8, wherein U' signifies —SO$_2$NH$_2$ or —SO$_2$R$_9$.

10. A compound of claim 9, wherein R$_2'$ signifies a chlorine atom in the 4-position of the phenyl ring to which it is attached, R$_1'$ signifies a methyl group in the 2-position of said phenyl ring, or hydrogen, and R$_3'$ signifies a chorine atom in the 5-position of said phenyl ring, or hydrogen.

11. A compound according to claim 9, wherein U' is —SO$_2$R$_9$.

12. A compound of claim 8, which, in free acid form, is of formula I″,

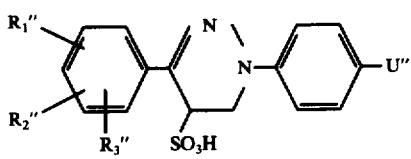

wherein
$R_1''$, $R_2''$ and $R_3''$, independently, signify hydrogen, chlorine or C$_{1-4}$alkyl,
U‴ is CO$_2$R$_6$, SO$_2$NH$_2$ or SO$_2$R$_9$.

13. A compound of claim 12, wherein any C$_{1-4}$alkyl as $R_1''$, $R_2''$ or $R_3''$ is methyl.

14. A compound of claim 13, wherein any C$_{1-4}$alkyl as R$_6$ or R$_9$ is C$_{1-2}$alkyl.

15. A compound of claim 14, which, in free acid form, is of formula I‴,

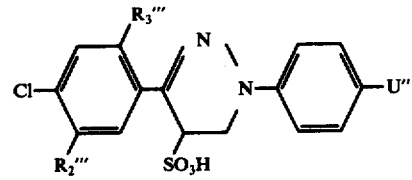

in which
$R_2'''$ signifies hydrogen, chlorine or methyl,
$R_3'''$ signifies hydrogen or methyl, and U″ signifies —CN, —CO$_2$R$_6'''$, —SO$_2$NH$_2$ or —SO$_2$R$_9'''$, in which R$_6'''$ signifies C$_{1-2}$alkyl, and R$_9'''$ signifies C$_{1-2}$alkyl.

16. A compound of claim 15, wherein U″ signifies —SO$_2$R$_9$.

17. A compound of claim 16, wherein R$_9$ signifies methyl.

18. A compound of claim 17, wherein either $R_2'''$ and $R_3'''$ are the same and signify hydrogen, or $R_2'''$ signifies chlorine and $R_3'''$ signifies methyl.

19. A compound of claim 18, which, in free acid form, is of formula

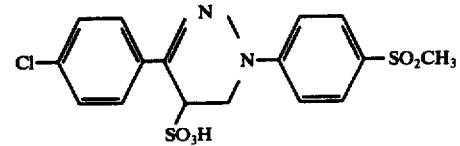

20. A compound of claim 18, which, in free acid form, is of formula

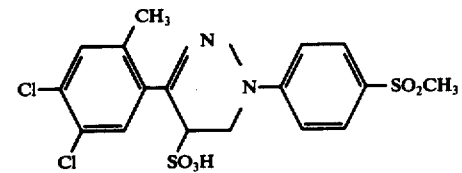

21. A compound of claim 1, in salt form.

22. A compound of claim 21, in alkali-metal, ammonium or alkylammonium salt form.

23. A compound of claim 22, wherein any ammonium or alkylammonium cation is of the formula $R_{15}R_{16}R_{17}R_{18}N+$, where $R_{15}$, $R_{16}$, $R_{17}$ and $R_{18}$, independently, signify hydrogen or C$_{1-4}$alkyl, unsubstituted or substituted by one or two hydroxy groups.

24. A compound of claim 22, in sodium salt form.

* * * * *